United States Patent
Dudai

(10) Patent No.: US 6,676,674 B1
(45) Date of Patent: Jan. 13, 2004

(54) GASTRIC BAND

(76) Inventor: Moshe Dudai, 13, Hadefna St., Jerusalem 95744 (IL)

( * ) Notice: Subject to any disclaimer, the term of this patent is extended or adjusted under 35 U.S.C. 154(b) by 0 days.

(21) Appl. No.: 09/526,757

(22) Filed: Mar. 16, 2000

(30) Foreign Application Priority Data

Mar. 17, 1999 (IL) .................................................. 129032

(51) Int. Cl.$^7$ .............................................. A61B 17/08
(52) U.S. Cl. ...................................... 606/151; 606/153
(58) Field of Search ................................ 606/151, 153, 606/155, 156, 157, 74, 232; 24/16 PB, 30.5 P

(56) References Cited

U.S. PATENT DOCUMENTS

| | | | |
|---|---|---|---|
| 3,111,945 A | * 11/1963 | Solbrig | 606/74 |
| 4,416,267 A | 11/1983 | Garren et al. | 128/1 R |
| 4,477,950 A | * 10/1984 | Cisek et al. | 24/30.5 P |
| 4,510,649 A | * 4/1985 | Yudis et al. | 24/16 PB |
| 4,592,339 A | 6/1986 | Kuzmak et al. | 128/1 R |
| 4,696,288 A | 9/1987 | Kuzmak et al. | 128/1 R |
| 4,950,285 A | * 8/1990 | Wilk | 24/16 PB |
| 5,226,429 A | 7/1993 | Kuzmak | 128/898 |
| 5,356,417 A | * 10/1994 | Golds | 24/16 PB |
| 5,395,343 A | * 3/1995 | Iscovich | 24/16 PB |
| 5,462,542 A | * 10/1995 | Alesi, Jr. | 606/151 |

FOREIGN PATENT DOCUMENTS

| DE | 197 51 733 A | 10/1998 |
|---|---|---|
| FR | 2 650 499 A | 2/1991 |

OTHER PUBLICATIONS

Forsell, P. et al., *A Gastric Band with Adjustable Inner Diameter for Obesity Surgery: Preliminary Studies*, Obesity Surgery, 3, 303–306 (1993).

* cited by examiner

*Primary Examiner*—Michael J. Milano
*Assistant Examiner*—Julian W. Woo
(74) *Attorney, Agent, or Firm*—Nath & Associates PLLC; Todd L. Juneau; Sheldon M. McGee

(57) ABSTRACT

A gastric band of a belt type is presented for attaching around a circumference of a patient's stomach, so as to define the diameter of the stomach opening. The band comprises outer and inner surfaces, wherein the inner surface engages the stomach, and at least the outer surface is formed by an elongated member substantially non-extendable along a longitudinal axis thereof. A through-going opening is made in the elongated member and is located so as to define an end portion of the band having a predetermined length. An opposite end portion of the band is shaped so as to be insertable into the through-going opening for adjusting a desired inner diameter of the band in its closed operating position and fastening the opposite end portion to the outer surface of the band.

5 Claims, 8 Drawing Sheets

US 6,676,674 B1

GASTRIC BAND

FIELD OF THE INVENTION

This invention relates to a gastric banding device that encircles a portion of the stomach to form a stoma opening of reduced diameter.

BACKGROUND OF THE INVENTION

Morbid obesity is associated with medical risks in terms of the development of additional diseases such as diabetes, hypertension, cardiac insufficiency and other socio-psychological problems, overall reducing life expectancy. Dietary management, psychiatric or dietary regiments are the first choice for treating morbid obesity, but as they depend on the goodwill of the patient, especially in the long run, these approaches often fail.

Various surgical approaches have been developed and used for treating morbid obesity. These include gastric bypasses, small bowel bypasses and stapling of portions of the stomach. The stapling techniques include horizontal and vertical stapling for reducing the volume of the stomach, as well as narrowing the stoma opening thus controlling the food intake of the stomach. However the latter approach, stapling, may not bring the desired results due to the fact that the staples frequently open or tend to cause perforations. Furthermore the stomach opening formed by staples widens over time, thus the effect is reduced or even eliminated.

A different approach to the problem specified above is described in U.S. Pat. No. 4,416,267, which discloses a method for treating obesity by placing an inflatable balloon into the stomach. Such a device displaces volume inside the stomach, thereby reducing the effective free volume of the gastric portion causing the individual to feel no need for additional food intake. The balloon is inflated in the stomach to a predetermined volume and is left there for a certain period of time after which it is easily removed. However, this procedure although being physically easy to implement and basically being non-surgical, may lead to harmful results. The inflated balloon in the stomach is in constant contact with gastric mucous, and such contact for an extended period of time may give rise to gastric ulcers and intestinal blockage.

Recently, another approach has been developed based on placing a physical means (i.e. a gastric band) outside the stomach. A gastric band is placed around the upper part of the stomach, thereby creating an altered stomach opening of a reduced diameter, resulting in the restriction of food intake into the digestive portion of the stomach. Such a gastric-banding technique is simple as compared to the above-mentioned balloon-based technique. However, this band has no means for adjusting its diameter to obtain the optimal diameter of the stomach opening.

Adjustable gastric bands have been developed, and disclosed for example in U.S. Pat. No. 4,592,339, as well as in "A Gastric Band with Adjustable Inner Diameter for Obesity Surgery", P. Forsell et al., Obes Surg., 1993, No. 3, pp. 303–306. According to this technique, the diameter of a belt-like band, when in a closed position thereof, may be adjusted. For this purpose, the band includes an inflatable portion in its interior part. Controllable inflating and deflating of this portion alters the stomach opening. Although this gastric band can retain the predetermined diameter of the stomach opening, obtaining of the proper opening is somewhat problematic.

U.S. Pat. No. 4,696,288 discloses a calibrating apparatus for using with a gastric band for controlling the diameter of the stomach opening by regulating the band's diameter. Such a gastric band is typically mounted with a laproscopic technique, disclosed for example in U.S. Pat. No. 5,226,429.

SUMMARY OF THE INVENTION

It is a main object of the present invention to provide a gastric band of a belt type, which can be attached to a patient's stomach in a safe manner and without damaging the stomach circumference.

It is a further object of the present invention to provide such a band which can be easily mounted on the stomach utilizing a laproscopic technique.

It is a still further object of the present invention to provide such a band that is easily enables its facile detectable by any suitable imaging means, thereby facilitating access to the band when additional surgical/laproscopic intervention is desired.

There is thus provided according to one aspect of the present invention, a gastric band for attaching around a circumference of a patient's stomach so as to define the diameter of the stomach opening, the band comprising:

(a) outer and inner surfaces, wherein the inner surface engages the stomach, and at least the outer surface is formed by an elongated member substantially non-extendable along a longitudinal axis thereof;

(b) a through-going opening made in said member and located so as to define an end portion of the band having a predetermined length; and (c) an opposite end portion of the band shaped so as to be insertable into said through-going opening for adjusting a desired inner diameter of the band in its closed operating position and fastening the opposite end portion to the outer surface of the band.

The gastric band is of a belt type, and also comprises a suitable fastening means, which may utilize a required number of stitches or the provision of bolt-and-nut arrangements on the band. The fastening means may also be in the form of teeth-like edges of the opposite end portion and a correspondingly shaped through-going opening.

The outer and inner surface may be formed either of the same material, or of different materials, provided that the material of the outer surface is substantially not-extendable. Preferably, at least the outer surface of the band is made of poly-tetra-fluoro-ethylene, known as Gortex. The material of the inner surface of the band engaging the stomach may be silicone. The band, when in the operation position thereof is such that its inner surface engaging the stomach has a substantially circular shape.

The predetermined length of the end portion is such as to enable the detection of the gastric band by a laproscopic inspection tool.

According to another aspect of the present invention, there is provided a system for laproscipically attaching a gastric band around a patient's stomach so as to define a certain diameter of the stomach opening, the system comprising a calibration device which is insertable into the stomach at a predetermined depth and comprises:

an upper portion having variable volume, and a lower projection-like portion having a diameter substantially equal to said certain diameter of the stomach opening to be defined by the band, the location of said projection-like portion when in the inserted position of the calibration device defining the location of the band with respect to the stomach;

said band comprising:
outer and inner surfaces, wherein the inner surface engages the stomach, and at least the outer surface is formed by an elongated member substantially non-extendable along a longitudinal axis thereof;
a through-going opening made in said member and located so as to define an end portion of the band having a predetermined length; and
an opposite end portion of the band shaped so as to be insertable into said through-going opening for adjusting a desired inner diameter of the band in its closed operating position and fastening the opposite end portion to the outer surface of the band.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figures 1A, 1B, 2:
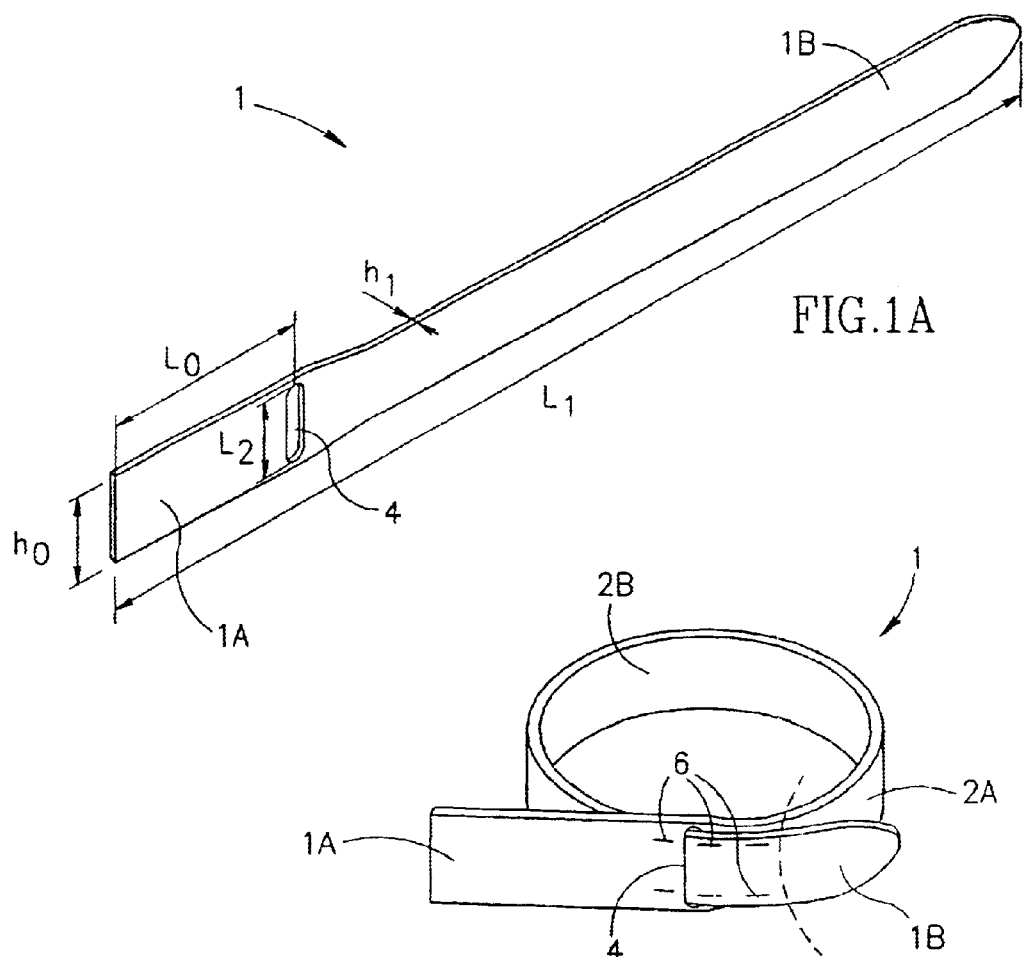
FIGS. 1a and 1b are schematic illustrations of a gastric band in its open and closed positions, respectively, constructed according to one embodiment of the invention.
FIG. 2 schematically illustrates the band of FIGS. 1a and 1b in its operation position being attached to the patient's stomach.

Referring to FIGS. 1a and 1b there is illustrated a gastric band, generally designated 1, constructed according to one embodiment of the invention. The band is typically an elongated-strap having two opposite end portions 1a and 1b. The portion 1b is substantially cone shaped, while the end portion 1a is formed with a through-going, substantially elliptically-shaped opening 4 displaced from the corresponding butt-end of the band 1 by a certain length $L_0$, the purpose of which will be described further below. For example, the band's dimensions may be as follows:

1) the length $L_1$ of the entire band is about 15 cm;
2) the length $L_0$ is about 3 cm;
3) the width $h_0$ of the band is 2 cm;
4) the thickness $h_1$ of the band is 2 mm; and
5) the long axis $L_2$ of the opening 4 is about 1–7 mm.

As clearly seen in FIG. 1b, the band 1 has outer and inner surfaces 2a and 2b, respectively. To attach the band 1 around a stomach (not shown here), the cone shaped end portion 1b passes through the opening 4, and is fastened along a corresponding location on the band by a suitable fastening means, for example by stitches 6. Thereafter, the free part of the end portion 1b is cut off by any suitable means, as shown in a dashed line. The opposite end portion 1a, whilst being optionally partly stitched to the band 1, extends away therefrom. The band 1 is made of a polymer material, which is substantially non-extendable along its longitudinal axes. For example, poly-tetra-fluoroylene (i.e. Gortex) can be used for manufacturing the band 1.

Turning now to FIG. 2, there is illustrated that, when in the operative position of the band 1 being attached around a stomach 10, the free end portion 1a protrudes from the band. It will be readily understood that such a protrusion would be easily detected by any suitable imaging means. This is a very important feature facilitating the access to the band when additional surgical/laproscopic intervention is desired As further seen in FIG. 2, the band 1 actually defines two portions 10a and 10b of the stomach 10, and defines the diameter of a so-called stomach opening (not seen here) underneath the band 1. The portions 10a and 10b are fastened to each other by stitches 12 or the like within the vicinity of the band 1, thereby fixing its relative location on the stomach. It should be noted that stitches 6, as well as the stitches 12, may be replaced by any other suitable fastening means.

Figure 3A:
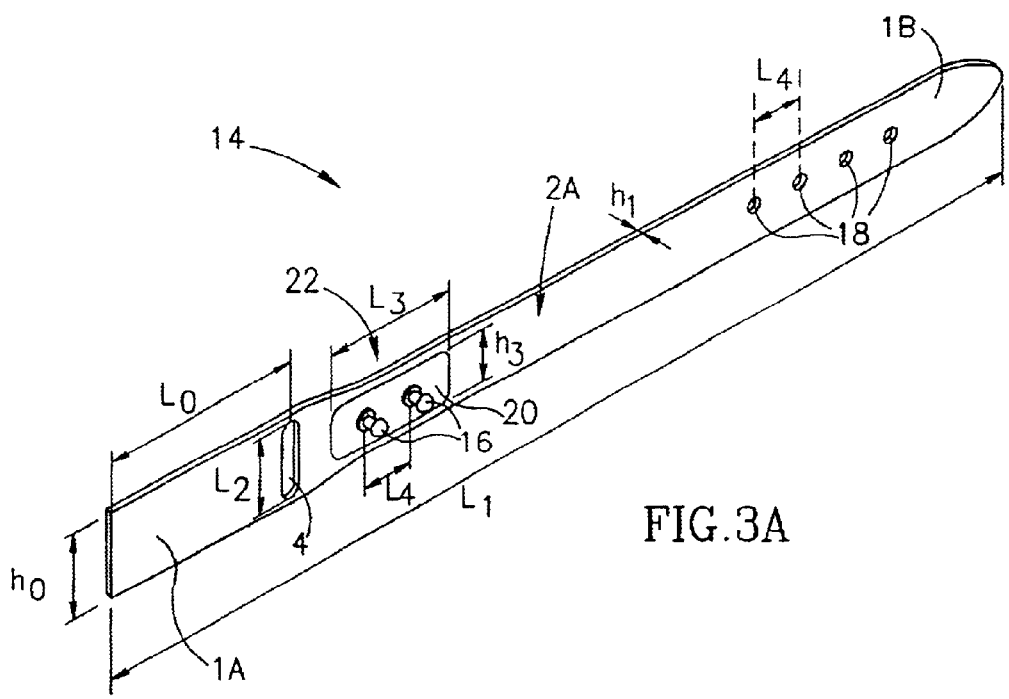
FIGS. 3a and 3b are schematic illustrations of a gastric band in its open and closed positions, respectively, constructed according to another embodiment of the invention.
Figure 3B:
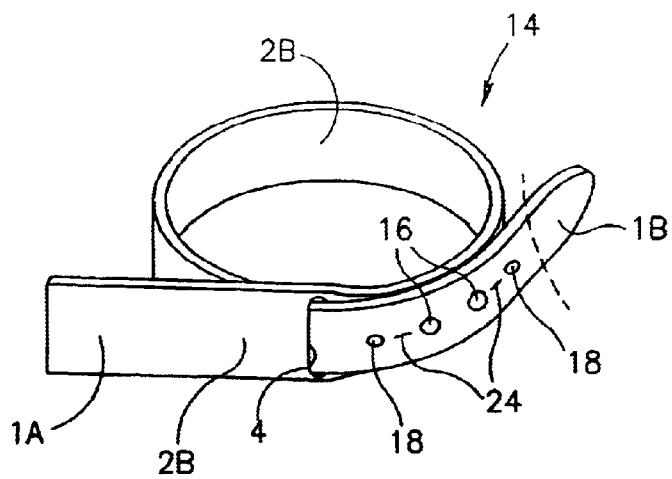

Reference is made to FIGS. 3a and 3b, illustrating a gastric band 14 in its opened and closed positions, respectively. The band 14 has somewhat different construction as compared to the band 1. To facilitate understanding, same reference numbers are used for identifying those components, which are identical in the bands 1 and 14. Here, at least one so-called "bolt-and-nut" arrangement is provided serving as the fastening means. To this end, as shown in the figures in a self-explanatory manner, spaced-apart mushroom-like bolts, generally at 16, project upwardly from the upper surface 2a. Consequently, holes 18 (four in the present example) are aligned along the longitudinal axis of the band in a spaced-apart parallel relationship. The diameter of the hole 18 corresponds to that of the bead portion of the mushroom-like bolt 16 to put the bolt-and-nut arrangement into its engaged position, thereby closing the band.

In this specific example, the bolts 16 project from a plate-like support 20, forming together an integral assembly, generally designated 22. The assembly 22 is attached to the upper surface 2a of the band 14 by stamping. The entire band, except for the assembly 22, may be made of a polymer material like Gortex, while the assembly 22 may be made of a substantially rigid silicone. The bolts 16 (and consequently two locally adjacent holes 18) are spaced from each other by the length $L_4$ of about 7 mm, the dimensions of the plate 20 being as follows: the length $L_3=2$ cm, and the width $h_3=12$ mm. As shown in FIG. 3b, after closing the band on the patient's stomach, two stitches 24 (or the like) are provided to ensure the fixed diameter of the band, and thereby of the stomach opening. Similarly to the previously described embodiments, the corresponding part of the end portion 1b is cut off, while the opposite part 1a protrudes from the band to be detectable.

Figure 4A:
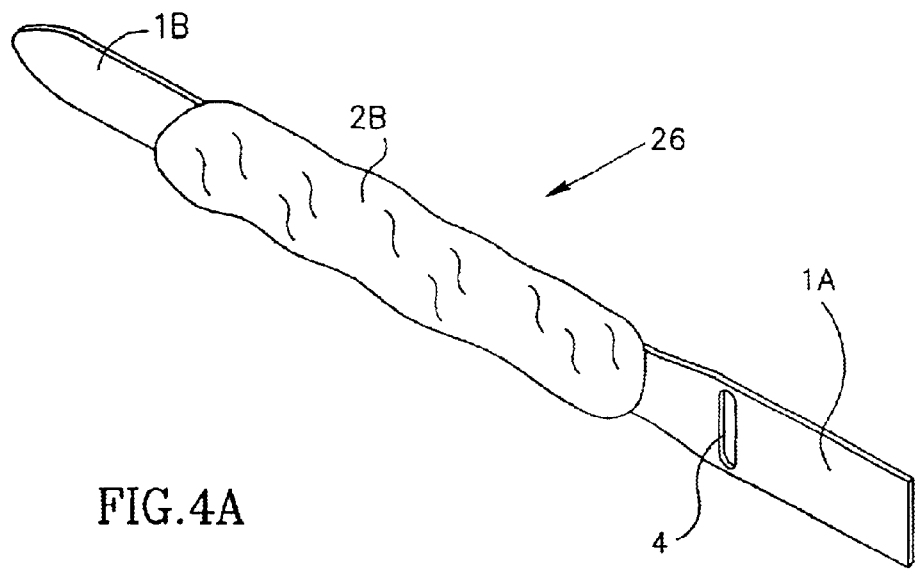
FIGS. 4a and 4b are schematic illustrations of a gastric band in its open and closed positions, respectively, constructed according to yet another embodiment of the invention.
Figure 4B:
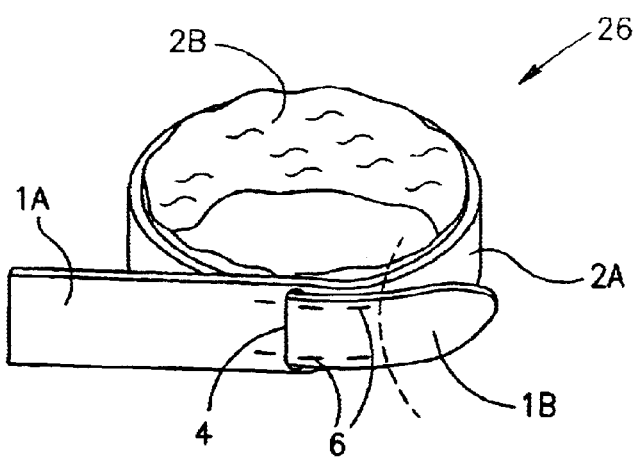

FIGS. 4a and 4b illustrate a gastric band, generally at 26, according to yet another embodiment of the invention. Similarly, same reference numbers are used for identifying those components, which are identical in the bands 1, 14 and 26. The band 26, in distinction to the bands 1 and 14, has its inner surface 2b formed of a relatively flexible material relative to that of the outer surface. For example, this may be implemented by coating a center part of the inner surface of the band 26 with silicone. As for the outer surface 2a of the band 26, as well as the inner surface thereof within the end portions, they are made of a substantially non-extendable material. The end portion 1a should be made of such a non-extendable material which is not too rigid in order not to harm the stomach, e.g. Gortex.

Figure 5A:
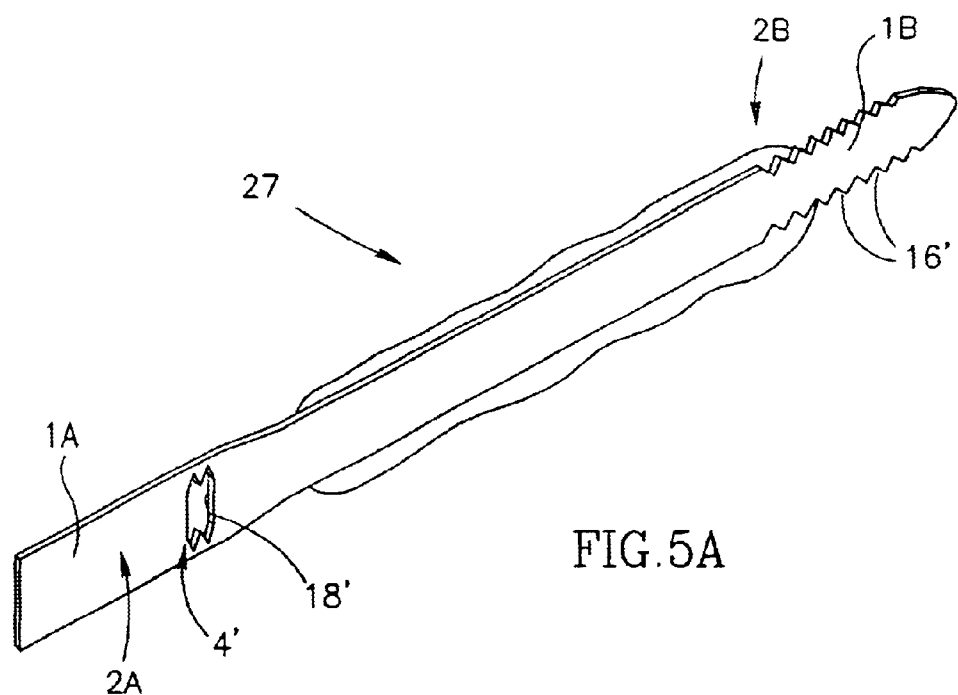
FIGS. 5a and 5b are schematic illustrations of a gastric band in its open and closed positions, respectively, constructed according to yet another embodiment of the invention.
Figure 5B:
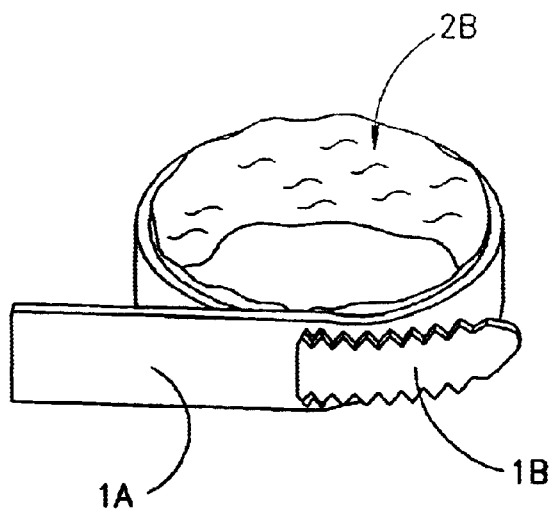

FIGS. 5a and 5b illustrate yet another construction of a gastric band 27 using the same reference numbers for identifying the common elements in the bands 1, 14, 26 and 27. In the band 27, similar to the band 26, the center part of its inner surface is formed with a substantially flexible material, e.g. flexible silicone, while the end portions are made of a non-extendable material. As for the fastening means, in the band 27 the end portion 1b is formed with teeth-like edges 16'. Consequently, a through-going opening 4' is shaped in a manner to define a slot 18' allowing a forward movement of the portion 1b through the opening 4', but preventing its sliding back out of the opening 4' in the operating (closed) position of the band 27. To this end, the 16 center part of the outer surface 2a, as well as the end portion 1b, are made of a substantially rigid material, e.g. rigid silicone. As indicated above, the opposite end portion 1a should be made of a substantially flexible material.

Figure 6A:
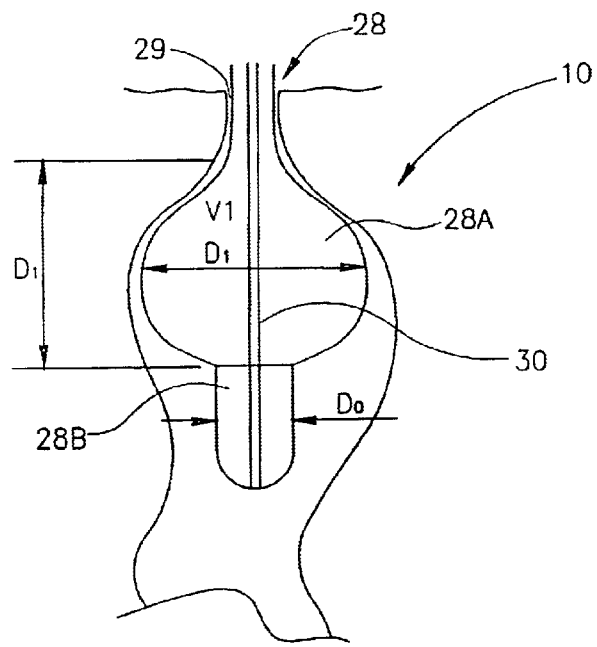
FIGS. 6a and 6b schematically illustrate two steps of a calibration procedure carried out prior to mounting the band on the stomach.
Figure 6B:
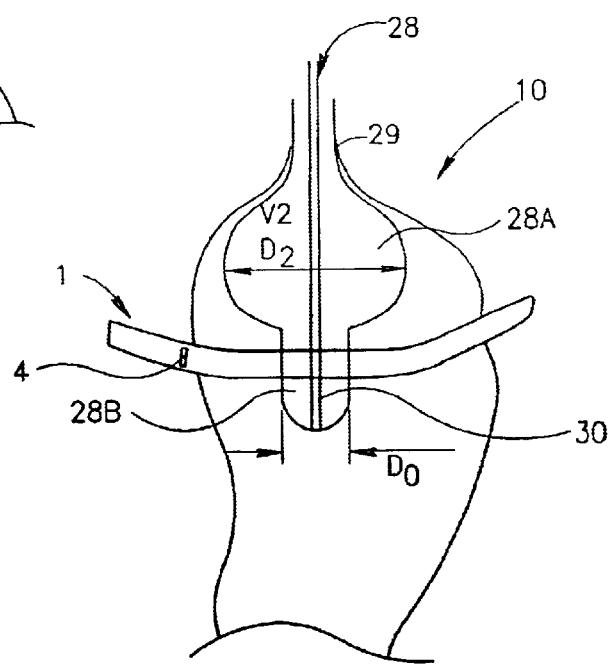

Reference is now made to FIGS. 6a and 6b illustrating two steps of a typically performed calibration stage for determining the desired diameter of the stomach opening and defining its location to mount a gastric band there.

To this end, a calibrating device, generally designated 28, is used. The construction and operation of such a calibration device are known per se, and therefore need not be described in detail, except to note the following. The device 28 comprises an upper, balloon-like portion 28a associated with a suitable pump, which is not specifically shown, and a lower projection 28bb having a substantially circular cross-section of the desired diameter $D_0$.

Upon inserting the device 28 inside the stomach 10 through a stomach inlet 29, the balloon-like portion 28a is inflated up to the volume $V_1$ corresponding to the diameter $D_1$ of the portion 28a, so as to substantially engage the inner circumference of the stomach 10. This maximum diameter $D_1$ of the portion 28a is determined in accordance with the inflating pressure.

Thereafter, the device is partially deflated to such a volume $V_2$ that corresponds to the diameter $D_2$ of the portion 28a, and pulled upwardly up to the inlet 29. Such a position of the device 28 having the known diameter $D_2$ of its balloon-like portion 28a actually allows for locating the projection 28b, thereby defining the location for mounting the gastric band. The calibrating device 28 also comprises a pipe 30 installed thereinside, serving for aspirating the stomach contents and checking whether the mounting of the band caused any damage to the stomach itself, as will be described more specifically further below with reference to FIG. 7f.

Figure 7A:
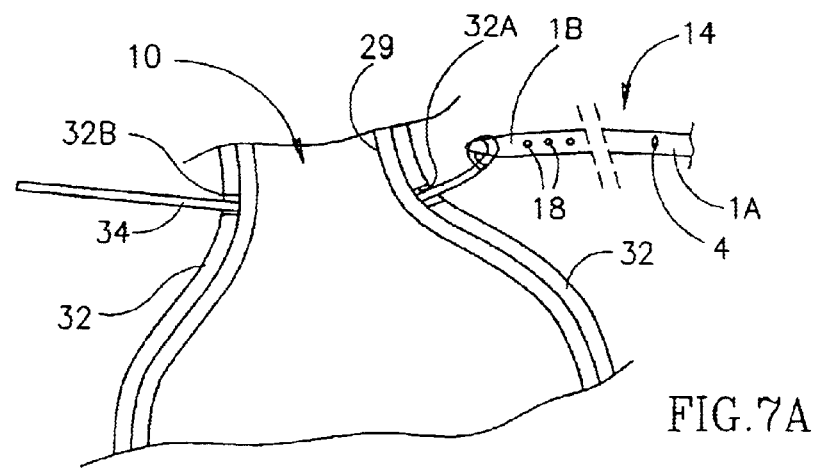
FIGS. 7a to 7f illustrates five sequential steps, respectively, of mounting the band of FIGS. 3a–3b onto the patient's stomach.
Figure 7B:
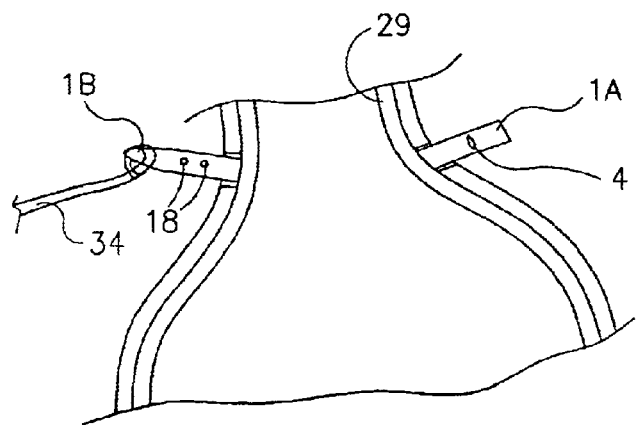

Referring to FIGS. 7a to 7f, there are illustrated the main operational steps for laproscopic mounting of the gastric band, for example constructed as described above with reference to FIGS. 3a and 3b, on the patient's stomach. As indicated above, the position of the projection 28b defines the exact location for mounting the band. Hence, it defines the convenient locations for cuttings 32a and 32b to be made in the stomach connecting tissue 32 at opposite sides of the stomach 10. An articulated gripping device 34 is typically used for mounting the gastric band on the stomach 10. FIG. 7a illustrates that the articulated gripping device 34 is sequentially pushed through the openings 32b and 32a, to clamp the cone shaped end portion 1b of the band 14. Then, by pulling the device 34, the band is threaded through the openings 32a and 32b, thereby engaging the back-side of the stomach (FIG. 7b).

Figure 7C:
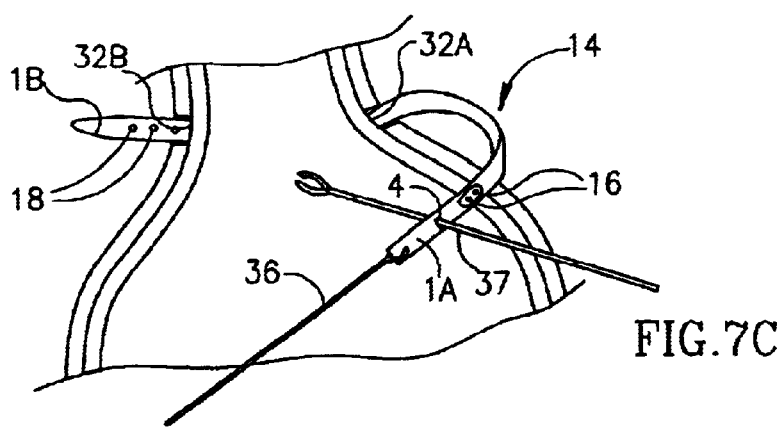
Figure 7D:
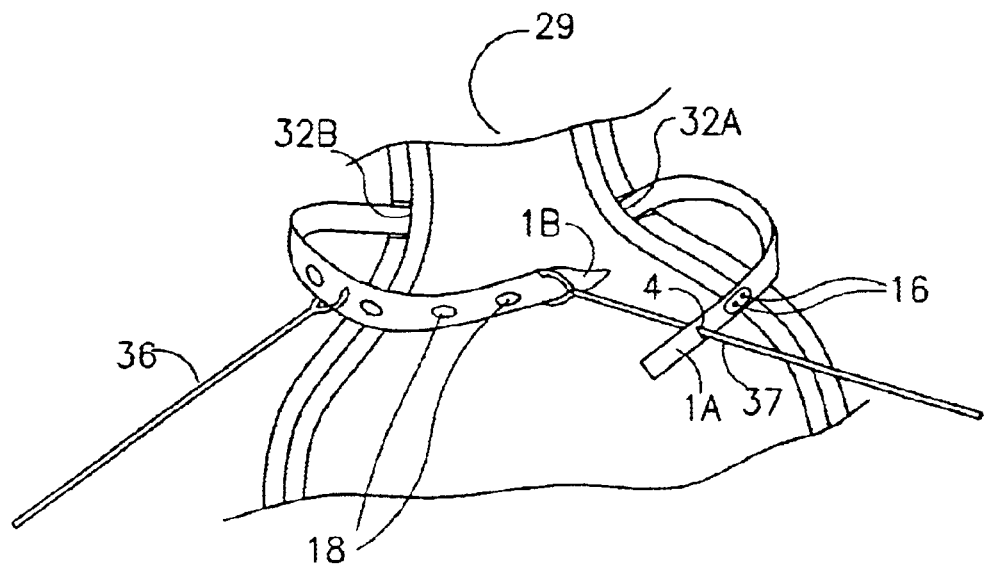
Figure 7E:
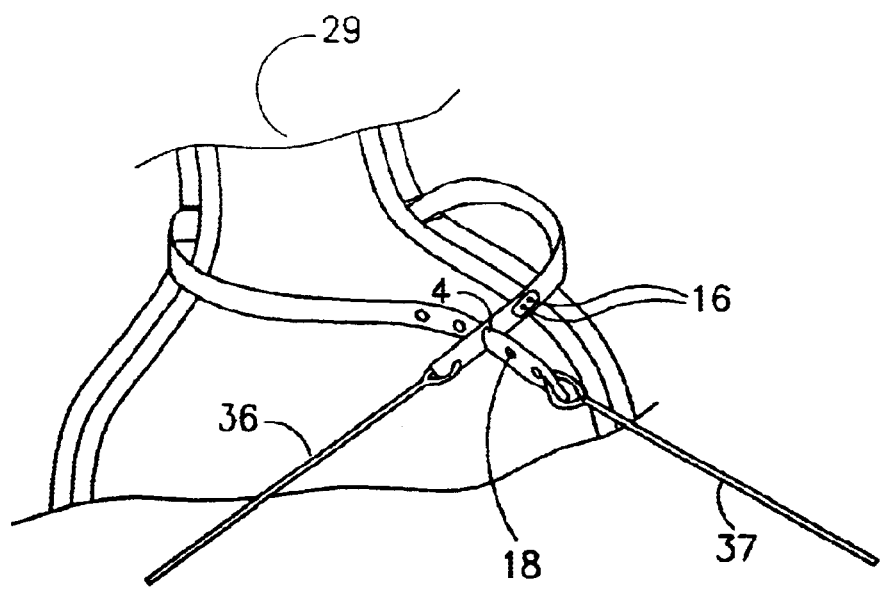
Figure 7F:
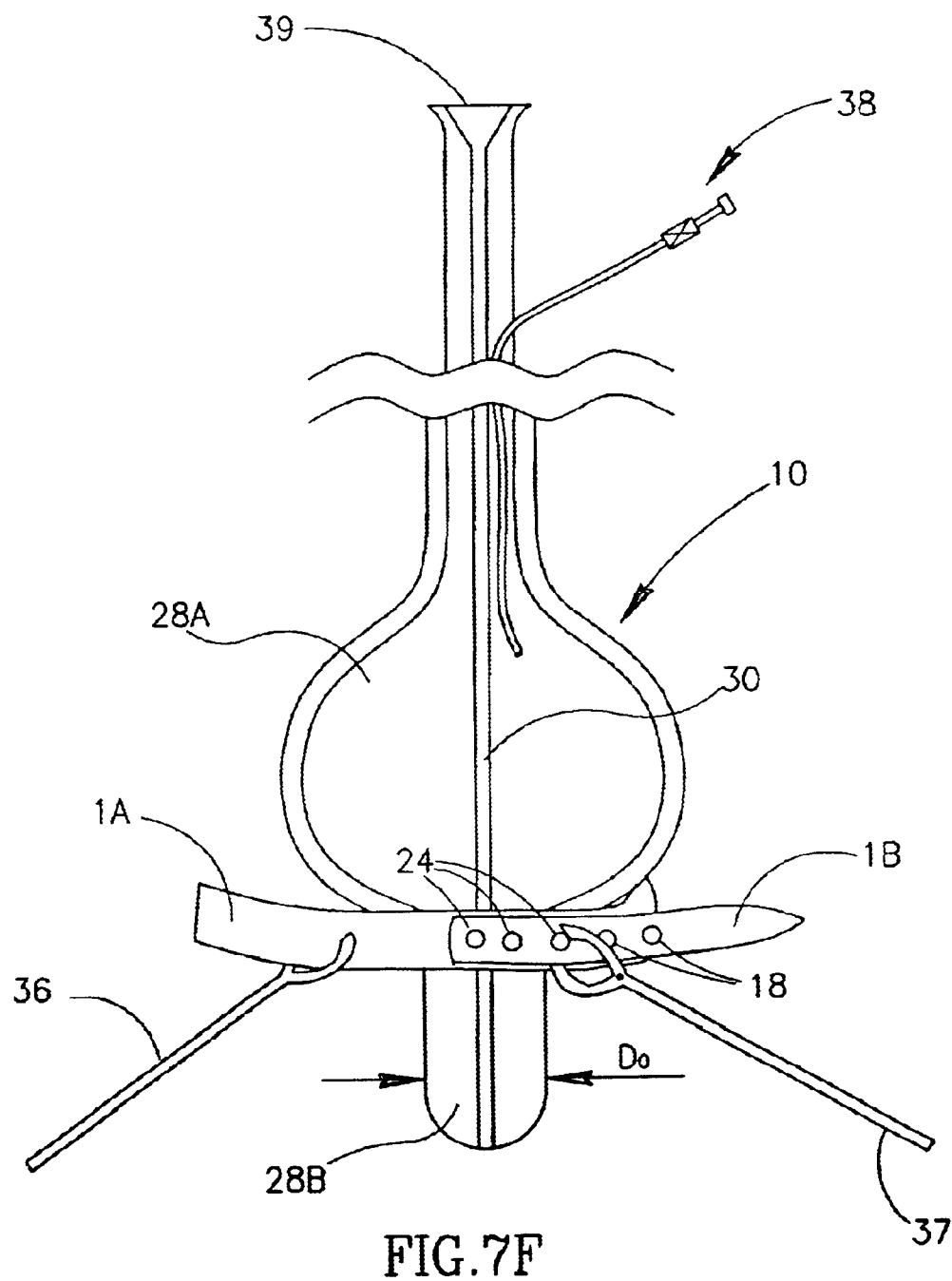

This having been done, a pair of gripping devices 36 and 37 are used for supporting the end portion 1a of the band, while the device 34 passes through the opening 4 and proceeds towards the cone shaped portion 1b (FIG. 7c). As shown in FIGS. 7d and 7e, by manipulating the gripping devices 36 and 37, the cone shaped end portion 1b is threaded through the opening 4 and pulled to close the band in a manner described above with reference to FIGS. 3a and 3b. The closed operating position of the band is illustrated in FIG. 7f.

After completing the mounting of the gastric band 14, a pair of stitches 24 are provided and, optionally, depending on the desired diameter, the end portion 1b is partly cut off. To check whether the entire operation did not damage the stomach and did not completely block the stomach opening, the following procedure is carried out. After the total deflation of the balloon 28a (through a suitable pump-valve assembly 38) and pulling of the calibrating device 28 upwardly towards the upper part of the paunch, a colored liquid is injected into the pipe 30 through an upper opening 39 of the device 28. It will be readily understood that the non-passage of this liquid into the stomach through the lower end of the pipe 30 indicates of the blockage of the stomach opening. Likewise, any dripping of the colored liquid out of the stomach would indicate of the dangerous condition of stomach perforation, which should immediately be treated.

Those skilled in the art will readily appreciate that various modifications and changes can be applied to the invention as hereinbefore exemplified without departing from its scope defined in and by the appended claims. For example, the gastric band may have any appropriate dimensions, providing it is capable of providing the desired diameter of the stomach opening and its free end portion is detectable by a suitable imaging system.

What is claimed is:

1. A non-inflatable gastric band mounting onto a patient's stomach outside the stomach, so as to fix a desired diameter of the band in its operating closed position to thereby adjust a desired diameter of the stomach opening and a volume of the stomach above the band defined by a separate calibrating device, the band being made of a soft non-extendable material and comprising:
    (a) outer and inner surfaces, wherein the inner surface engages the stomach when in an operating position of the band mounted on the stomach;
    (b) a through-going opening at a location spaced from a butt-end of the band a predetermined distance to define an extended end portion of the band of a predetermined length, such that, when the band is closed, said end portion freely protrudes front the band;
    (c) an opposite end portion of the band shaped so as to be insertable into said through-going opening for adjusting a desired inner diameter of the band in its closed operating position and fastening said opposite end portion to the outer surface of the band upon establishing the desired diameter;
        said extended end portion and said opposite portion serving for gripping the band while mounting it onto the stomach and adjusting the diameter of the band to bring it into its operating closed position, said extended free protruding end portion of the band enabling detection of the band while in the operative position thereof mounted on the stomach and enabling gripping the band for readjusting the diameter of the stomach opening after the band is brought into its operating position; and (d) a fastening means for fastening said opposite end portion of the band to the outer surface of the band to bring the band into its operating closed position, said fastening means allowing locking and real zing the band while adjusting the inner diameter of the band to bring the band into said operating position;

wherein said fastening means comprises at least two stitches applied to the band.

2. A non-inflatable gastric band mounting onto a patient's stomach outside the stomach, so as to fix a desired diameter of the band in its operating closed position to thereby adjust a desired diameter of the stomach opening and a volume of the stomach above he band defined by a separate calibrating device, the band being made of a soft non-extendable material and comprising:

(a) outer and inner surfaces, wherein the inner surface engages the stomach when in an operating position of the band mounted on the stomach;

(b) a through-going opening at a location spaced from a butt-end of the band a predetermined distance to define an extended end portion of the band of a predetermined length, such that, when the band is closed, said end portion freely protrudes from the band;

(c) an opposite end portion of the band shaped so as to be insertable into said through-going opening for adjusting a desired inner diameter of the band in its closed operating position and fastening said opposite end portion to the outer surface of the band upon establishing the desired diameter;

said extended end portion and said opposite portion serving for gripping the band while mounting it onto the stomach and adjusting the diameter of the band to bring it into its operating closed position, said extended free protruding end portion of the band enabling detection of the band while in the operative position thereof mounted on the stomach and enabling gripping the band for readjusting the diameter of the stomach opening after the band is brought into its operating position;

wherein said outer and inner surfaces of the band are formed of a first material and a second material, respectively, wherein said first material and said second material are constructed of different substances and said second material being not too rigid in order not to harm the stomach.

3. The gastric band according to claim 1, wherein said second material comprises silicone.

4. The gastric band according to claim 2, wherein said first material comprises poly-tetra-fluoro-ethylene.

5. The gastric band according to claim 2, wherein said second material comprises silicone.

* * * * *